United States Patent [19]

Thakur

[11] Patent Number: 5,308,603
[45] Date of Patent: May 3, 1994

[54] METHOD TO DIRECTLY RADIOLABEL ANTIBODIES FOR DIAGNOSTIC IMAGING AND THERAPY

[75] Inventor: Mathew L. Thakur, Cherry Hill, N.J.

[73] Assignee: Thomas Jefferson University, Philadelphia, Pa.

[21] Appl. No.: 591,964

[22] Filed: Oct. 2, 1990

Related U.S. Application Data

[62] Division of Ser. No. 499,790, Mar. 27, 1990, Pat. No. 5,011,676.

[51] Int. Cl.$^5$ ........................ A61K 49/02; A61K 43/00
[52] U.S. Cl. ................................ 424/1.490; 530/391.5; 530/402
[58] Field of Search .................... 530/391.5, 402; 424/1.1

[56] References Cited

U.S. PATENT DOCUMENTS

| | | | |
|---|---|---|---|
| 4,305,922 | 12/1981 | Rhodes | 424/1.1 |
| 4,401,646 | 8/1983 | Rhodes et al. | 424/1.1 |
| 4,416,865 | 11/1983 | Rhodes et al. | 424/1.1 |
| 4,424,200 | 1/1984 | Crockford et al. | 424/1.1 |
| 4,472,371 | 9/1984 | Burchiel et al. | 424/1.1 |
| 4,478,815 | 10/1984 | Burchiel et al. | 424/1.1 |
| 4,645,660 | 2/1987 | Takahashi et al. | 424/1.1 |
| 4,652,400 | 3/1987 | Paik et al. | 424/1.1 |
| 4,837,003 | 6/1989 | Nicolotti | 424/1.1 |
| 4,851,515 | 7/1989 | Bonnyman et al. | 534/14 |
| 4,917,878 | 4/1990 | Thakur | 424/1.1 |
| 5,053,493 | 10/1991 | Pak et al. | 424/1.1 X |
| 5,061,641 | 10/1991 | Shochat et al. | 424/1.1 X |
| 5,128,119 | 7/1992 | Griffiths | 424/1.1 |

OTHER PUBLICATIONS

Chem. Abstract. vol. 91, No. 19, abstract 153,599f (1978), Winchell et al., Nuclear Medizin Suppl., 16, 165-167.

Khaw, B. A., Strauss, W. and Carvalho, A. et al., *Tc-99m Labeling of Antibodies to Cardiac Myosin Fab and to Human Fibrinogen*, J. Nucl. Med. 23, 1011-109, 1982.

Paik, C. H., Pham. L. N. B., Hong, J. J. et al., *The Labeling of High Affinity Sites of Antibodies With Tc-99m*, Int. J. Nucl. Med. and Biol. 12, 3-8, 1985.

Thakur, M. L., Richard, M. D., and White F. W., III, *Monoclonal Antibodies as Agents For Selective Radiolabeling of Human Neutrophils*, J. Nucl. Med. 29, 1817-1825, 1988.

Franz, J., Volkert, W. A., Barefield, E. K., et al., *The Production of Tc-99m Labeled Conjugated Antibodies Using a Cyclam-Based Bifunctional Chelating Agent*, Int. J. Nucl. Med. Biol. 14, 569-572, 1987.

Fritzber, A. R., Kasina, S., Reno, J. M. et al., *Radiolabeling Antibodies Using $N_2S_2$ Ligands*, J. Nucl. Med. 27, 957-958, 1986.

Lin et al., *Use of Fe(II) or Sn(II) Alone for Technetium Labeling of Albumin*, J. Nucl. Med., vol. 12, No. 5, pp. 204-10.

Eckelman, et al., $^{99m}$*Tc-Human Serum Albumin*, J. Nucl. Med., vol. 12, No. 11, pp. 707-710 (1971).

Pettit, *Improved Protein Labeling by Stannous Tartrate Reduction of Pertechnetate*, J. Nucl. Med., vol. 21, No. 1, pp. 59-62 (1980).

Huang et al., *Detection of Bacterial Endocarditis with Technetium-99m-Labeled Antistaphylococcal Antibody*, J. Nucl. Med., volo. 21, No. 8, pp. 783-786 (1980).

Rhodes et al., *Technetium-99m labeling of Murine Monoclonal Antibody Fragments*, J. Nucl. Med., vol. 27, No. 5, pp. 685-693 (1986).

(List continued on next page.)

*Primary Examiner*—Robert L. Stoll
*Assistant Examiner*—John M. Covert
*Attorney, Agent, or Firm*—Woodcock, Washburn, Kurtz, Mackiewicz & Norris

[57] ABSTRACT

The invention is a novel method and kit for directly radiolabeling proteins such as antibodies or antibody fragments for diagnostic and therapeutic purposes. The method comprises incubating a protein-containing solution with a solution of sodium ascorbate; adding a required quantity of reduced radionuclide to the incubated protein. A kit is also provided wherein the protein and/or reducing agents may be in lyophilized form.

8 Claims, No Drawings

OTHER PUBLICATIONS

Sundrehagen et al., *Formation of $^{99m}$Tc-Immunoglobulin G Complexes Free from Radiocolloids, Quality Controlled by Radioimmunoelectrophoresis*, European J. Nucl. Med., vol. 7, pp. 549–552 (Spring 1982).

Blok et al., *A New Method for Protein Labeling With $^{99m}$Tc*, Nucl. Med. Biol., vol. 16, No. 1, pp. 11–16 (1989).

Stiegman et al., *The Importance of the Protein Sulfhydryl, Group in HSA Labeling with Technetium–99m*, Proceedings of 22nd Annual Meeting, J. Nucl. Med., vol. 16, No. 6.

Liang et al., *Serum Stability and Non–Specific Binding of Technetium–99m Labeled Diaminodithiol for Protein Labeling*, Nucl. Med. Biol., vol. 14, No. 6, pp. 555–561 (1987).

Schwartz, A. and Steinstrabber, A. *A Novel Approach to Tc–99m Labeled Monoclonal Antibodies*, J. Nucl. Med. 28, 721, 1987.

Pak et al., *A Rapid and Efficient Method for labeling IgG antibodies with Tc–99m and Comparison to Tc–99m FAB' Antibody Fragments*, J. Nucl. Med., vol. 30, p. 793 (1989).

Del Rosario et al., *Site–Specific Radiolabeling of Monoclonal Antibodies with Biotin/Streptavidin*, Nucl. Med. Biol., vol. 16, pp. 525–527 (1989).

Cleland, *Dithiothreitol, A New Protective Reagent for SH Groups*, Biochemistry, vol. 3, pp. 480–482, (1966).

Hawkins et al., *Resistance fo Direct Tc-99m–Protein Bond to Transchelation*, Antibody, Immunoconjugates, and Radiopharmaceuticals, vol. 3, No. 1 (1990).

Jones, A. G., Orvig, C., Trop, H. S. et al., *A Survey of Reducing Agents for the Synthesis of Tetraphenylarsoniumoxotechnetium (Ethnedithiolate) From Tc-99m Pertechnetate in Aqueous Solution*, J. Nucl. Med. 21, 279–281, 1980.

Thakur et al., *Determination of Reduced Disulfide Groups in Monoclonal Antibodies*, BioTechniques, vol. 8, No. 4 (1990).

Szent-Gyorgyi, *A Textbook of Pharmacology, Toxicology, and Therapeutics for Physicians and Medical Students*, Third Edition, Chapter 74, (1928) *Water–Soluble Vitamins*.

METHOD TO DIRECTLY RADIOLABEL ANTIBODIES FOR DIAGNOSTIC IMAGING AND THERAPY

The invention described herein was made in the course of work under a grant or award from the Department of Energy and an NIH Cancer Research training grant.

This is a division of application Ser. No. 499,790, filed Mar. 27, 1990, now U.S. Pat. No. 5,011,676.

This invention was disclosed in Disclosure Document No. 232220 filed Sep. 14, 1989.

BACKGROUND OF THE INVENTION

The invention described herein was made in course of, or under U.S. Department of Energy Grant DE-OF-G2-85 and ER-60295 and a NIH Cancer Research Training Grant 05137-10.

The major thrust of the prior art concerning the use of radiolabeled monoclonal antibodies (Mabs) is focused on the development of their applications in imaging and therapy. Evidence suggests that Tc-99m possesses ideal characteristics for imaging and Re-186 or Re-188 for therapy. However, the procedures for labeling Mabs with these radionuclides remain inefficient and cumbersome. Unless the labeling processes are made simple, efficient and reliable, the use of Mabs for diagnostic imaging will remain restricted.

Technetium-99m possesses the attractive characteristics of convenience, inexpensiveness, low radiation dose, and suitability for planar and single photon emission computerized tomography (SPECT) imaging. There has been a continuous development of technology to incorporate Tc-99m in all molecules intended for diagnostic imaging applications. Monoclonal antibodies are no exception. Since Tc-99m has only a 6 hour half-life, in most cases the biological half-life of Tc-99m labeled antibody will be determined by the half-life of Tc-99m and not by the clearance time of the IgM, IgG or fragmented antibody. It is for these reasons that TC-99m continues to be the favorite radionuclide for most imaging applications of Mabs.

Indirect labeling of Mabs with Tc-99m via bifunctional chelating agents (BFCA) such as DTPA, cyclam, and diaminodithio ($N_2S_2$) compounds is well known in the art. A number of investigators have labeled antibodies with TC-99m via the use of BFCAs. Khaw, B. A., Strauss, W. and Carvalho, A. et al., Tc-99m *Labeling Antibodies to Cardiac Myosin Fab and to Human Fibrinogen*, J. Nucl. Med. 23, 1011-109, 1982; Paik, C. H., Pham, L. N. B., Hong, J. J. et al., *The Labeling of High Affinity Sites of Antibodies With Tc-99m*, Int. J. Nucl. Med. and Biol. 12, 3-8, 1985; Thakur, M. L., Richard, M. D., and White, F. W., III, *Monoclonal Antibodies as Agents For Selective Radiolabeling of Human Neutrophils*, J. Nucl. Med. 29, 1817-1825, 1988;,Franz, J., Volkert, W. A., Barefield, E. K., et al. *The Production of Tc-99m Labeled Conjugated Antibodies Using a Cyclam-Based Bifunctional Chelating Agent*, Int. J. Nucl. Med. Biol. 14, 569-572, 1987; and Fritzlier, A. R., Kasina, S., Reno, J.M. et al., *Radiolabeling Antibodies Using $N_2S$ Ligands*, J. Nucl. Med. 27, 957-958, 1986. Perhaps the most prominent method among them uses the diaminodithio compound as a BFCA. However, even this method requires a lengthy and cumbersome procedure that has prompted researchers to investigate direct labeling methods.

Direct labeling methods offer the advantages of 1) providing higher specific activity (mCi/mg); 2) eliminating the need for conjugation with a bifunctional chelating agent; 3) being less likely to alter the immunospecificity of the Mab; 4) being more likely to be adaptable to an instant "kit" labeling technique; and 5) being useful for labeling antibodies with radionuclides such as Re-186 or Re-188 for therapy.

Human serum albumin has been labeled with Tc-99m by the direct tin reduction method since 1971. The method was published by Lin et al., *Use of Fe(II) or Sn(II) Alone for Technetium Labeling of Albumin*, Journal of Nuclear Medicine, Vol. 12, No. 5, pp. 204–10, and modified by Eckelman et al., $^{99m}TC$-*Human Serum Albumin*, Journal of Nuclear Medicine, Vol. 12, No. 11, pp. 707–710 (1971). The method was adapted for labeling antibodies by Pettit *Improved Protein Labeling By Stannous Tartrate Reduction of Pertechnetate*, Journal of,Nuclear Medicine, Vol. 21, No. 1, pp. 59–62 (1980); Huang et al. *Detection of Bacterial Endocarditis with Technetium-99m-Labeled Antistaphylococcal Antibody*, Journal of Nuclear Medicine, Vol. 21, No. 8, pp. 783–786 (1980); and Rhodes et al., *Technetium-99m labeling of Murine Monoclonal Antibody Fragments*, Journal of Nuclear Medicine, vol 27, No. 5, pp. 685–693 (1986). At least in one case (Rhodes) the resulting labeled product has been reported to be unstable, requiring an elaborate system for purification of the antibody. Sundrehagen et al. , *Formation of $^{99m}Tc$-Immunoglobulin G Complexes Radioinmunoelectrophoresis*, European Journal.of Nuclear Medicine, Vol. 7, pp. 549–552 (Spring 1982), appreciating that the tin used in all these methods leads to the formation of Tc-99m-Sn-colloid, used a concentrated hydrochloric acid and gentisic acid reduction method for labeling immunoglobulin with Tc-99m. In order to avoid the colloid formation of Tc-99m, Blok et al., *A New Method for Protein Labeling With $^{99m}Tc$*, Nucl. Med. Biol., Vol. 16, No. 1, pp. 11–16 (1989), used a combination of dimethylformamide and 5M HCl in which Tc-99m was heated at 140° C. for 4 hours. The reduced Tc-99m was then extracted in CHCl evaporated to dryness, and incubated with antifibrin antibody for 1 hour at 40° C. However, these methods are lengthy, cumbersome, and are not adaptable to an instant kit procedure.

Stiegman et al., *The Importance of the Protein Sulfhydryl Group in HSA Technetium-99m*, Proceedings of 22nd Annual Meeting, J. Nucl. Med., Vol. 16, No. 6, suggested that the mechanism of Tc-99m binding was related to sulfhydryl groups. There are approximately 70 cysteine amino acid residues per IgG molecule, leading to approximately 175 disulfide bonds in an IgM molecule, approximately 35 in IgG, and approximately 25 in F(ab')$_2$. In the Fab fragment, there may be as many as 12 groups per molecule.

Liang et al., *Serum Stability and Non-Specific in of Technetium-99m Labeled Diaminodithiol for Protein Labeling*, Nucl. Med. Biol., Vol. 14, No. 6, pp. 555–561 (1987), suggested the importance of the helical structure of antibodies for the preservation of the Mab specificity and i=unologic activity. However, Rhodes demonstrated that reducing disulfide bonds to sulfhydryl groups not only allowed them to label murine Mab fragments with Tc-99m, but also preserved the immunoreactivity of the protein. This reduction was achieved by incubating 600 μg of antibody with 5 mM SnCl$_2$ for 21 hours. The product was then lyophilized, ready for adding Tc-99m pertechnetate. Presumably, the excess of SnCl$_2$ reduced Tc-99m for binding to the sulfhydryl groups. Following a 30 minute incubation, the reaction mixture was passed through a purification column designed to eliminate pertechnetate ions and other technetium impurities. Schwartz, A. and Steinstrabber, A., *A Novel Approach to Tc-99m Labeled Monoclonal Antibodies*, J. Nucl. Med. 28, 721, 1987, considered that an excess of SnCl$_2$ at pH 6-7, may lead Tc-99m to the formation of colloid. Schwartz et al. achieved the reduction of antibody disulfide groups with 2-mercaptoethanol (ME). Excess reagent was eliminated by molecular gel filtration and the protein was lyophilized. Reduction of pertechnetate was achieved by the use of commercial pharmaceutical kits such as pyrophosphate, which contains SnCl$_2$. This solution was then added to the lyophilized protein to allow Tc-99m to exchange from the phosphate groups to the sulfhydryl groups.

In our hands, the Rhodes et al. and the Schwartz et al. methods result in a labeling efficiency of about 65% and 44%, respectively. Both methods also require further purification to eliminate unbound Tc-99m. These methods, therefore, are appealing and improvement over bifunctional chelating agent methods. In a routine radiopharmacy setting, however, these methods are less than ideal because of the required purification steps. Recently Pak et al., *A Rapid and Efficient Method for labeling IgG Antibodies with Tc-99m and Comparison to Tc-99m FAB' Antibody Fragments*, Journal of Nuclear Medicine, Vol. 30, p. 793 (1989) and Del Rosario et al., *Site-Specific Radiolabeling of Monoclonal Antibodies with Biotin/Streptavidin*, Nucl. Med. Biol., Vol, 16, pp. 525-527 (1989) used DTT (dithiothreitol) to reduced antibody disulfide groups and label them with Tc-99M. Pak et al. used a commercial glucoheptonate kit which contains SnCl$_2$ to reduce Tc-99m. DTT and its isomer DTE (dithioerrythritol) were prepared by Cleland, *Dithiothreitol, A New Protective Reagent for SH Groups*, Biochemistry, vol. 3, pp. 480-482, 1966) in 1964, and used to reduce protein disulfide groups.

In addition 2-ME has a very unpleasant, strong smell of sulfur. DTT and DTE also contain sulfur but have a less intense smell. Some patients are allergic to such compounds. For this reason, unlike ascorbic acid excess of these compounds must be removed from the proteins prior to administration to a patient.

Labeling of Tc-99m to sulfhydryl groups of antibodies has been designated by Paik et al. as high affinity but low capacity binding. Neither Rhodes et al. or Schwartz et al. show any data as to how many disulfide groups, if any, are involved and how the reduction affects the structural integrity and immunoreactivity of the antibody. Relative stability of the labeled tracer with respect to other competing chelating agents was also undetermined. A recent article by Rhodes group (Hawkins et al., *Resistance of Direct Tc-99m-Protein Bond to Transchelation*, Antibody, Immunoconjugates, and Radiopharmaceuticals, Vol. 3, No. 1 (1990)) show Tc-99m-s-protein bond is stable.

Jones, A. G., Orvig, C., Trop, H. S. et al., *A Survey of Reducing Agents for the Synthesis of Tetraphenylarsonium-oxotechnetium (Ethanedithiolate) From Tc-99m Pertechnetate in Aqueous Solution*, J. Nucl. Med. 21, 279-281, 1980, disclose that sodium dithionite in the range of pH 11-13 gives quantitative yields of the required technetium complex through the 100% reduction of Tc-99m rapidly at room temperature. He also reported that at pH 11-13, the results were consistently quantitative.

U.S. Pat. No. 4,305,922 (Rhodes) teaches labeling proteins with Tc-99m by ligand exchange using a Sephadex column (chelating agent). A mixture of Tc-solution and stannous solution are poured into the top of the column. The protein to be labeled is then added and ligand exchanged occurs as the Tc-99m ions preferentially migrate from the chelating agent to the protein. The labeled protein is then washed through the column and recovered.

U.S. Pat. No. 4,401,646 (Rhodes et al.) discloses a method and apparatus for purifying materials radiolabeled with Tc-99m by passage through a filtration column which contains a reducing agent, colloidal stannous phthalate, anti-oxidant and a particulate solid substrate capable of binding reduced Tc and of retaining insoluble Tc. Useful anti-oxidants include gentisic acid, ascorbic acid, tartaric acid, or mixtures thereof. In this case, ascorbic acid is used to reduce the radioactive Tc only.

U.S. Pat. No. 4,416,865 (Rhodes et al.) discloses urokinase, streptokinase or fibrinokinase labeled with Tc-99m, $^{131}$I or $^{123}$I for localization of thromboembolic diseases. The enzymatic protein is combined with the nuclide in a basic solution containing ferric chloride and ascorbic acid, and the pH adjusted to acidic conditions to produce a radiopharmaceutical. In this case, ascorbic acid is used to reduce the radioactive Tc only.

U.S. Pat. No. 4,424,200 (Crockford et al.) discloses methods for radiolabeling proteins with Tc-99m in a reducing environment by incubating a source of stannous ion with a protein in the presence of a buffering composition (a mixture of an alkali metal biphtalate and alkali metal tartrate) at pH 4.5-8.5 for at least 15 hours at a temperature where the protein is not denatured.

U.S. Pat. No. 4,478,815 (Burchiel et al.) discloses a composition and method for detecting cancer with technetium labeled antibody fragments. The composition is an F(ab')$_2$ or F(ab) Fragment of antibody to hCG, hCG-α, hCG-β or hCG-like material or other tumor specific or associated molecules including CEA, AFP, human melanoma associated antigens labeled with Tc-99m. The radiolabeled fragment is injected intravenously, accumulates at tumor sites, and is detected by scintigraphy. A double antibody approach is also taught wherein a tumor specific antibody in the form of IgG, F(ab')$_2$ or F(ab) is administered to a patient intravenously, followed by administration of a radiolabeled antibody in the form of F(ab')$_2$ or F(ab) which is reactive with the first antibody. The radiolabeled reagents are formed under reducing conditions to minimize or prevent the reversible reaction by which the Tc-99m becomes free of the antibody fragment. The Tc-99M labeled antibody fragment may be prepared by acidic, basic or neutral (ligand exchange) radiolabeling techniques.

U.S. Pat. No. 4,652,400 (Paik et al.) discloses a direct labeling method comprising reacting a reduced radioisotope of rhenium or technetium with an antibody in the presence of diethylebnetriaminepentaacetic acid (DTPA). The DTPA inhibits binding of the radioisotopes to nonstable binding sites.

U.S. Pat. No. 4,472,371 (Burchiel et al.) discloses the labeling of radiolabeling antibodies with technetium. The Tc is reduced by stannous ions prior to labeling and the protein is also reduced using stannous chloride or stannous fluoride.

U.S. Pat. No. 4,645,660 (Takahashi et al.) discloses the reduction of a radioisotope carrier with ascorbic acid in order to increase its chelating capacity. In this case, ascorbic acid is used to reduce the radioactive Tc only.

U.S. Pat. No. 4,837,003 (Nicolotti) discloses a labeling process utilizing a coupling agent that complexes with a radionucleotide. The coupling agent is covalently bound to the Ab through sulfhydryl groups produced by mild reduction of the disulfide linkages. Reducing agents which are disclosed include 2-mercaptoethanol and, as the preferred agent, cysteine.

U.S. Pat. No. 4,851,515 (Bonnyman et al.) discloses a labeling process using the nitrodotetrahalotechnetium-99m anion and at least partial reduction of the disulfide linkages to sulfhydryl residues by use of a reducing agent such as dithiothreitol (DTT).

SUMMARY OF THE INVENTION

The present invenniion provides an improved method to directly label proteins such as antibodies or serum protein with a radiolabel such as Tc-99m, Re-186 or Re-188. The first step involves the reduction of the protein's disulfide bonds to sulfhydryl groups that allow efficient bonding of the radiolabel. The disulfide reducing agent is ascorbic acid. The radiolabel is separatly reduced. In this method, a protein-containing solution is allowed to react with Na-ascorbate solution, pH 6.5 (AA), in the protein:AA molar ratio of 85-8500. Following incubation, a required quantity of a reducing agent, such as dithionite or stannous chloride, is used to reduce the radiolabel, at a basic pH. This method provides a number of advantages including: stability upon incubation with DPTA, human serum and cysteine; the immunospecificity of the protein as determined by specific antigen interaction assay is unchanged; and purification is not required. Ascorbic acid, in it's oxidized, dehydrogenated form is vitamin C, which is non-toxic, non-odorous and need not be eliminated. A kit suitable for preparation of the radiolabeled antibodies is also provided.

None of the prior art methods teach or suggest the direct labeling method of the present invention. The importance of a technique that allows labeling of proteins with a radionuclide quickly and reliably, by an instant kit type of procedure is a significant improvement in the art.

It is therefore an object of the invention to provide a method for directly radiolabeling proteins for diagnostic imaging and therapy.

It is a further object of the invention to provide a novel method to label an IgG, IgM or F(ab')$_2$ antibody fragment with Tc-99m, Re-186 or Re-188.

It is another object of the invention to provide a kit for labeling proteins useful for diagnostic imaging and therapy.

Further objects and advantages of the invention will become more apparent in light of the following detailed discussion of the invention.

DETAILED DESCRIPTION OF THE INVENTION

To overcome the problems described above, the present invention 1) uses an agent which will effectively reduce the protein without the need to eliminate any excess and 2) uses an TJU-323 PATENT agent that will reliably reduce the radionuclide and will minimize colloidal formation.

The presence of excess of the disulfide bond reducing agent prevents the reoxidation of sulfhydryl groups, maintaining their ready availability for Tc-99m binding. At a 1:3500 ratio only 2.7±0.2% of the available S-S groups are reduced. Thakur et al., *Determination of Reduced Disulfide Groups in Monoclonal Antibodies*, BioTechniques, Vol. 8, No. 4 (1990). This excess of reducing agent, under appropriate chemical conditions, and with the correct oxidation-reduction potential, prevents reoxidation of reduced Tc-99m once it is introduced to the antibody.

Colloid formation not only prevents reduced Tc-99m from binding to the protein but also requires a step to eliminate it. An agent and the chemical conditions that will minimize colloid formation are of an obvious advantage.

The present invention satisfies both criteria resulting in enhanced labeling yields with elimination of the need for separation procedures. This method is adaptable to a kit comprising the reduced protein in lyophilized form and lyophilized chemicals ready to receive radionuclide solution to produce the reduced radionuclide. The reduced radionuclide is then added to the lyophilized antibody. Preferably, alternatively one vial containing reduced antibody and a radionuclide reducing agent ready to receive the radionuclide could be produced. Following incubation, (5-30 minutes, 22° C.-37° C.) and a quality control assay, the labeled antibody is ready for administration to a patient. The kit format and procedure is especially useful for the preparation of Tc-99m, Re-186 or Re-188 labeled proteins.

The Disulfide Reducing Agent

In 1928, Szent-Gyorgyi, *A Textbook of Pharmacology, Toxicology, and Therapeutics for Physicians and Students*, Third Edition, Chapter 74, *Water-Soluble Vitamins*, separated a "powerful reducing agent" in crystalline form from adrenal. Because of its physiological role in the prevention of scurvy, the compound was called ascorbic acid (AA). AA serves an important function in maintaining SH-activated enzyme systems in. their reduced form. The agent also serves as a hydrogen donor and in its oxidized dehydrogenated form serves as a vitamin. In sodium salt form it can be administered to humans by intramuscular or intravenous injections. These properties make AA useful,in this invention because this agen t 1) can reduce the Mab disulfide bonds to sulfhydryl groups, 2) maintain the activated SH groups in their reduced form, and 3) does not require elimination because the excess or the oxidized portion of it can only serve a helpful role in the body.

The Tc-99m Reducing Agent

Sodium dithionite is the preferable agent to reduce Tc-99m. That is because the agent is readily soluble in water or normal saline (pH 5-6). At pH 11, the solution remains without colloid formation for a longer period of time than does SnCl$_2$, the commonly used reducing agent, under similar conditions. At pH 10-11, dithionite solutions ranging in concentrations from 1 mg to 50 mg per ml can be stored for longer than 48 hours without formation of colloid. The pH 11 buffer consists of 0.05M sodium bicarbonate solution, to which 0.1 M NaOH is added to adjust the pH. Sodium dithionite readily dissolves in this buffer and remains in solution without the formation of colloid for longer than 48 hours when protected from air or oxygen. This allows sufficient time for lyophilization and incubation time. Up to 200 μg of Na-dithionite have been used to reduce several mCi of Tc-99m in up to 200 μl Tc-99m solution.

Larger volumes of Tc-99m can be used. The incubation time at 22° C. is no longer than 5 minutes. Since the antibody solution in reduced form is rendered at pH 5-6, the final pH after the addition of the reduced Tc-99m is 7.9 to 8.2. Na-dithionite in pH 11 buffer is thus the preferred agent to reduce Tc-99m for labeling with Mab.

The following examples illustrate the present invention and are not intended to limit the same.

EXAMPLE 1

Preparation of Labeled Antibodies

Three IgM neutrophil specific antibodies (anti-SSEA-1, B.40.1, B.37.2.1), three IgG and one F(ab')$_2$ antibodies were labeled. The SSEA-1 antibody was obtained from RhoMed, Albuquerque, N. Me. and B.40.1 and B.37.2.1 from the Wistar Institute, Philadelphia, Penna. Depending upon the number of tests to be performed, 25 to 100 μg antibody solution were incubated for one hour at 22° C. with Na-ascorbate solution, pH 6.5 (AA), in the Mab:AA molar ratio of 85 to 8500. Following incubation, a required quantity of dithionite reduced Tc-99m, at pH 11 was added and the reaction mixture was further incubated for 1 hour at 22° C. The solutions were then subjected to quality control and immunospecificity tests as described in the following examples.

EXAMPLE 2

Reduction of Tc-99m

Tc-99m, eluted freshly from Medi-Physics generators was used. Typically, a known quantity of sodium dithionite ($Na_2S_2O_4$) was dissolved in a known volume of 0.05M sodium bicarbonate solution to which was added nitrogen purged 0.1 M solution of NaOH to adjust the pH to 11. The final concentration of dithionite solution was 10 mg/ml. This solution was added to a known volume of Tc-99m solution in such a way that the final concentration of dithionite was 0.6 to 0.8 μg/μl of the reaction mixture which totaled 60-70 μl in volume. The reaction was allowed to proceed for 5 minutes at 22° C. Initially, the Tc-99m solution was checked for reduction using instant thin layer chromatography (ITLC). Strips (1 cm×12 cm) cut from silica gel impregnated glass fiber sheets (Gelman Sciences Inc., Ann Arbor, Mich.) were used as a stationary phase and 0.15 M NaCl as a mobile phase. In this system, reduced Tc-99m remains at the point of application and the heptavalent, unreduced Tc-99m migrates to the solvent front. The radioactivity was then added to the antibody ready for labeling. The colloid formation, if any, of the Tc-99m was examined under a light microscope, by centrifugation, and by 0.22 μ Millipore filtration or using HSA impregnated ITLC and ethanol:ammonia:water (2:1:5) as a solvent. (Colloid Rf:0.0; bound Rf:1.0.) Thrall, et al., *Clinical Comparison of Cardiac Blood Pool Visualization with Technetium-99m Red Blood Cells Labeled in Vivo and with Technetium-99m Human Serum Albumin*, Journal of Nuclear Medicine. Vol. 19, pp. 796-803 (1978). These tests were performed at the end of the incubation period and, occasionally, 3 to 6 hours later.

EXAMPLE 3

Determination of Tc-99m Labeling Efficiency

The commonly used ITLC was used on each reaction mixture, as described above. Additionally, each mixture was also subjected to HPLC analysis. The HPLC system is equipped with a U.V. (280 nm) monitor, a NaI(Tl) radioactivity detector, and dual pen chart recorder. Water's protein Pak 300 SW column and 0.2M phosphate buffer in 0.15 M NaCl, pH 6.8 as an eluent were used. The flow rate was 0.5 ml/minute. The pressure varied between 100-300 PSI and the chart speed was 0.25 cm/minute. 2 to 10 μl samples were injected. Additionally, samples were filtered through 0.22 μ Cameo filters to eliminate any colloid, subjected to Centricon-30 filtration to eliminate any unreduced Tc-99m, and the protein bound activity collected was further analyzed on HPLC. On each occasion, the HPLC samples gave a single radioactivity peak corresponding to the protein optical density peak. The results of the percentage of the protein bound radioactivity, with respect to the total present in the reaction mixture, indicated that even at the lowest protein to AA molar ratio (1:85), greater than 80% of the added reduced Tc-99m activity was protein bound, reaching 1004 at the ratio of approximately 5000 and above. Greater than 954 labeling efficiency can be achieved with the protein to AA molar ratio of 1:3500 (35 μg AA for 50 μg IgM).

EXAMPLE 4

Stability of Te-99m Labeled Antibody When Challenged With Cysteine, DPTA and Human Serum The IgM antibodies were labeled with Tc-99m, as above, checked with ITLC and HPLC for labeling efficiency and freedom from unbound Tc-99m. The labeled Mabs were then challenged with such Tc-99m avid agents as cysteine, DTPA, and freshly prepared human serum. For each agent, 1:250, 1:500 and 1:1000 (antibody:agent) molar ratios were used and each incubated at 37° C. for 30 minutes. Each sample was then subjected to HPLC analysis. The resulting elution patterns clearly separated Mab, each from cysteine, DTPA or serum indicating that all 100% Tc-99m remained bound to the antibody, except in the case of 1000 molar excess of cysteine. In that case,-approximately 20% of the Tc-99m was bound to cysteine and approximately 80% remained protein bound.

EXAMPLE 5

Determination of Immunoreactivity

The immunoreactivity of the IgM antibodies labeled with Tc-99m by this technique was determined by the ability of the labeled antibodies to label freshly prepared human neutrophils. Antibodies labeled with either In-111 or with Tc-99m via the c-DTPA bifunctional chelating agents served as controls. Antibodies labeled by art known techniques were also tested. For each antibody preparation, equal number of cells in duplicate and equal quality of antibody samples was used. The calculated quantities of antibody were added so that the total antibody molecules would not exceed 50% of the available cell surface antigens ($5.1 \times 10^5$/cell). Incubation was carried out at 22° C. for 30 minutes, following which cells were washed twice with autologous plasma. Radioactivity associated with cells and remaining in the supernatant and the washing was counted, and the results expressed as t cell bound activity as follows:

| Sample | % Cells Bound |
| --- | --- |
| 111-In-c-DTPA (control) | 75 ± 2 |
| Tc-99m-SnCl$_2$ | 66 ± 1 |
| Tc-99m-2-ME | 63 ± 2 |

-continued

| Sample | % Cells Bound |
|---|---|
| Tc-99m-DTT | 62 ± 3 |
| Tc-99m-DTE | 62 ± 2 |
| Tc-99m-AA | 84 ± 1 |

The association of Tc-99m activity bound to an equal number of platelets having nonspecific-antigen was only 16±0.5%. Similarly, only 8±1.5% of the nonspecific protein was bound to an equal number of human neutrophils.

EXAMPLE 6

Evaluation of Tc-99m Labeled Proteins for Localization of Inflammation: Comparison with I-125-TNT-1 and Ga-67 Citrate Tc-99m labeled polyclonal IgG, antinucleus antibody TNT-1, and human serum albumin (HSA) were investigated in mice bearing inflammation in right thigh induced by i.m. administered of 50 μl turpentine (TP) or 1:1 mixture of 10xE8 *E. Coli* and *Enterococci* (EC) using Ga-67, and I-125-TNT-1 as controls. Tc-99m was labeled by the above-described direct, disulfide reduction technique and I-125 labeled using Iodogen. Each preparation was analyzed by HPLC and ITLC and given IV (20 μg, known μCi) to groups of 5 mice with each type of inflammation. Four or 24 hours later mice were imaged, sacrificed and tissues dissected. At 4 hours TP abscess/muscle ratios for Ga were 4.8±2.1, I-125-TNT-1 4.3±1, Tc-99m-TNT-1 3.5±1.8, Tc-99m-IgG 3.9±0.6 and Tc-99m-HSA 4.3±1. With EC these were 2.6±0.6, 3.3±0.5, 3.4±0.08, 3±1.1 and 4.1±0.6, respectively. At 4 hours liver uptake was highest (25.7±8.9 and 16.5±10.6) for Tc-99m IgG and lowest (6±5.1 and 4.8±3.20) for Tc-99m-TNT-1, which was similar to those of I-125-TNT-1. For 24 hour groups, no dramatic increase in inflammation/tissue ratios was noted. Results suggest a) distribution of I-125-TNT-1 is similar to Tc-99m-TNT-1 indicating no alteration in biological behavior of protein following Tc-99m labeling, b) Tc-99m-TNT-1, IgG and HSA are equivalent to Ga-67 for imaging inflammatory foci but may allow abscess imaging at 4 hour post administration.

| | TNT-1-125 | | TNT-1-Tc-99m | |
|---|---|---|---|---|
| | TP | EC | TP | EC |
| Liver | 6.8 ± .9* | 10.1 ± .85** | 6 ± 5.1* | 4.8 ± 3.2** |
| Abscess/ Muscle | 4.3 ± 1.1* | 3.3 ± .5** | 3.5 ± 1.8* | 3.4 ± .8** |

TP = Turpentine
EC = Microorganic
Liver *P>0.76 ** P>004
Abscess/Muscle *,** P>0.75

EXAMPLE 7

Evaluation of Tc-99m-TNT-1-F(ab')₂ for Imaging Tumors: Comparison with 1–125-TNT-1F(ab')₂

TNT-1 is a murine antibody that recognizes antigens released from degenerated cells. This has been labeled with I-131 and used for localization of tumors with necrotic centers (Feng-Ming Chen et al., *Tumor Necrosis Treatment of ME-186 Human Cervical Carcinoma Model with $^{131}$I-Labeled TNT-1 Monoclonal Antibody*, Cancer Research, Vol. 49, pp. 4578–4585, Aug. 15, 1989. F(ab')₂ fragmented TNT-1 was obtained from Dr. Epstein (USC-LA), labeled with Tc-99m using the ascorbic acid technique, and given i.v. (approximately 20 μg and 40 μCi) to a group of mice, bearing experimental teratocarcinoma grown to no more than 1 cm in size in the right thigh of BALB/C mice. TNT-1-F(ab')₂ labeled with I-125 was given to an additional group of tumor bearing mice served as a control. Four hours later, Tc-99m animals Were imaged (I-125, low energy gamma cannot be imaged) with a gamma camera coupled to a pinhole collimator and a Microdot imager. All animals were then sacrificed, tissues dissected and radioactivity associated with tissues was counted. Results were expressed as percent administered dose per gram of tissue and tumor to tissue ratios. With both agents, tumor/muscle ratios of 10.04±4.4 and 10.94±3.07 (P<0.5) were obtained and tumors- were clearly delineated. Distribution of the two agents was similar (statistically insignificant) except that Tc-99m blood values were lower (P<0.001) and kidney values higher (P<0.005) than I-125-TNT-1. The rapid blood clearance may help enhance image quality and the rapid excretion further reduces the radiation burden which is already low because of the short half-life of Tc-99m.

| Four Hour Tissue Distribution in Balb/c Mice | | |
|---|---|---|
| | TNT-1-F(ab')₂-Tc-99M % Ad. Dose/G | TNT-1-F(ab')₂-I-125 % Ad. Dose/G |
| Bearing Experimental Tumor | | |
| Urine | 129.3% ± 41.6 | 59.3% |
| Blood | 5.1% ± 1.7* | 12.8% ± 1.6* |
| Kidneys | 25.3% ± 7.1* | 7.2% ± 0.55* |
| Intestine | 1.2% ± 0.54 | 2.7% ± 0.50 |
| Muscle | 0.5% ± 0.11 | 0.7% ± 0.06 |
| Tumor | 4.7% ± 1.4* | 8% ± 2.5* |
| Spleen | 14.8% ± 1.2 | 4.1% ± 0.21 |
| Lungs | 6.1% ± 1.7 | 9.4% ± 2.8 |
| Liver | 15.8% ± 10.9* | 4% ± 0.66 |
| Heart | 2.1% ± 0.2 | 3.9% ± 0.25 |
| Tumor/Tissue Ratio | | |
| Tumor/Liver | 0.20 ± 0.07 | 1.99 ± 0.43 |
| Tumor/Blood | 0.76 ± 0.25 | 0.63 ± 0.17 |
| Tumor/Muscle | 10.04 ± 4.4 | 10.94 ± 3.07 |

*Blood P<0.0001; Kidneys P<0.005; Tumor P>0.11, Liver P>0.12

Obviously many modifications and vartiations of the present invention are possible in light of the above teachings. It is, therefore, to be understood that within the scope of the appended claims the invention may be practiced otherwise than as specifically described.

What is claimed is:

1. A kit suitable for directly labeling a protein with radionuclides for use in diagnostic imaging and therapy comprising a quantity of protein and a quantity of sodium ascorbate sufficient to reduce a controlled number of disolfide groups in the protein to sulfhydryls; and a quantity of sodium dithionite or stannous chloride sufficient to reduce the labeling radionuclide.

2. The kit of claim 1 wherein said protein is an antibody or an antibody fragment.

3. The kit of claim 2 wherein said antibody is an IgG antibody.

4. The kit of claim 2 wherein said antibody is an IgM antibody.

5. The kit of claim 2 wherein said antibody fragment is an F(ab')₂ or F(ab) fragment.

6. The kit of claim 1 wherein said protein is serum protein.

7. The kit of claim 1 wherein said protein and said sodium ascorbate are lyophilized.

8. The kit of claim 1 wherein said reducing agent is lyophilized.

* * * * *

UNITED STATES PATENT AND TRADEMARK OFFICE
CERTIFICATE OF CORRECTION

PATENT NO. : 5,308,603                              Page 1 of 4

DATED : May 3, 1994

INVENTOR(S) : Thakur

It is certified that error appears in the above-identified patent and that said Letters Patent is hereby corrected as shown below:

On title page, under "OTHER PUBLICATIONS" delete "volo." and insert therefor --Vol.--.

Column 1, Line 17, please delete "DE-OF-" and insert therefor --DE-FO- --.

Column 1, Line 49, after "Tc-99m Labeling", please insert --of--.

Column 1, Line 61, please delete "Fritzlier," and insert therefor --Fritzber--.

Column 1, Lines 62 and 63, please delete "$N_2$SLigands" and insert therefor --$N_2S_2$ Ligands--.

Column 2, Line 29, after "G Complexes" please insert -- Free from Radiocolloids, Quality Controlled by --.

Column 2, Line 30, please delete "Radioinmunoelectrophoresis," and insert therefor -- Radioimmunoelectrophoresis,--.

Column 2, Line 41, please delete "CHCI" and insert therefor --$CHCl_3$,--.

Column 2, Line 47, please insert --Labeling with-- after "Group in HSA".

Column 2, Line 56, please delete "Non-Specific in of" and insert therefor --Non-Specific Binding of--.

UNITED STATES PATENT AND TRADEMARK OFFICE
CERTIFICATE OF CORRECTION

PATENT NO. : 5,308,603
DATED : May 3, 1994
INVENTOR(S) : Thakur

It is certified that error appears in the above-indentified patent and that said Letters Patent is hereby corrected as shown below:

Column 2, Line 61, please delete "i=unologic" and insert therefor --immunologic--.

Column 5, Line 7, please delete "coupling,agent" and insert therefor --coupling agent--.

Column 5, Line 20, please delete "inve niion" and insert therefor --invention--.

Column 5, Line 26, please delete "separatly" and insert therefor --separately--.

Column 5, Line 66, please delete "TJU-323 PATENT".

Column 6, Line 34, please insert --Medical-- before "Students,".

Column 6, Line 40, please delete "in." and insert therefor --in--.

Column 6, Line 45, please delete "useful.in" and insert therefor --useful in--.

Column 6, Line 46, please delete "agen t" and insert therefor --agent--.

Column 8, Line 19, please delete "1004" and insert therefor --100%--.

Column 8, Line 21, please delete "954" and insert therefor --95%--.

UNITED STATES PATENT AND TRADEMARK OFFICE
CERTIFICATE OF CORRECTION

PATENT NO. : 5,308,603
DATED : May 3, 1994
INVENTOR(S) : Thakur

It is certified that error appears in the above-identified patent and that said Letters Patent is hereby corrected as shown below:

Column 8, Line 25, please delete "Te-99m" and insert therefor --Tc-99m--.

Column 8, Line 40, please delete "case,-approximately" and insert therefor --case, approximately--.

Column 8, Line 62, please delete "as t cell" and insert therefor --as % cell--.

Column 9, Line 9, please delete "platalets" and insert therefor --platelets--.

Column 9, Line 58, please delete "with 1-125-" and insert therefor --with I-125- --.

Column 9, Line 63, please delete "ME-186" and insert therefor --Me-180--.

Column 10, Line 3, please delete "BALB/C" and insert therefor --BALB/c--.

Column 10, Line 6, please delete "Were" and insert therefor --were--.

Column 10, Line 14, please delete "(P<0.5)" and insert therefor --(P>0.5)--.

UNITED STATES PATENT AND TRADEMARK OFFICE
CERTIFICATE OF CORRECTION

PATENT NO. : 5,308,603
DATED : May 3, 1994
INVENTOR(S) : Thakur

It is certified that error appears in the above-indentified patent and that said Letters Patent is hereby corrected as shown below:

Column 10, Line 14, please delete "tumors-" and insert therefor --tumors--.

Column 10, Line 41, please delete "vartiations" and insert therefor --variations--.

Column 10, Line 51, please delete "disolfide" and insert therefor --disulfide--.

Signed and Sealed this

Eighth Day of November, 1994

Attest:

BRUCE LEHMAN

Attesting Officer

Commissioner of Patents and Trademarks